US011534078B2

(12) United States Patent
Tang et al.

(10) Patent No.: US 11,534,078 B2
(45) Date of Patent: Dec. 27, 2022

(54) STEERABLE GUIDING SHEATH WITH RING ELECTRODES AND RELATED METHOD OF CONSTRUCTION

(71) Applicant: Biosense Webster (Israel) Ltd., Yokneam (IL)

(72) Inventors: Raymond Yue-Sing Tang, Rosemead, CA (US); Brian Raze, Yorba Linda, CA (US); Mark Griffin, Louisville, KY (US); Eric Gratz, Louisville, KY (US); Cortney Young, Louisville, KY (US); Eric E. Bielefeld, Floyds Knobs, IN (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 1186 days.

(21) Appl. No.: 15/372,313

(22) Filed: Dec. 7, 2016

(65) Prior Publication Data

US 2018/0153434 A1 Jun. 7, 2018

(51) Int. Cl.
*A61B 5/053* (2021.01)
*A61M 25/00* (2006.01)
(Continued)

(52) U.S. Cl.
CPC ......... *A61B 5/0538* (2013.01); *A61M 25/005* (2013.01); *A61M 25/0012* (2013.01);
(Continued)

(58) Field of Classification Search
CPC ..... A61B 5/042; A61B 5/0538; A61B 5/6851; A61B 5/6852; A61M 25/0012;
(Continued)

(56) References Cited

U.S. PATENT DOCUMENTS 5,727,715 A * 3/1998 McKenna ........... B05B 11/3052 222/189.09
5,891,114 A 4/1999 Chien et al.
(Continued)

FOREIGN PATENT DOCUMENTS

CN 102232869 A 11/2011
CN 104363848 A 2/2015
(Continued)

OTHER PUBLICATIONS

European Patent Office Search Report for Application No. EP 17205699.6, dated May 4, 2018; 8 pages.
(Continued)

*Primary Examiner* — Eun Hwa Kim
(74) *Attorney, Agent, or Firm* — Lewis Roca Rothgerber Christie LLP

(57) ABSTRACT

A guiding sheath has a braided layer for improved deflection characteristics and ring electrodes for electrical sensing, mapping and visualization, wherein lead wires for the ring electrodes are passed through lumened tubing position under the braided layer in a proximal portion of the guiding sheath shaft and above the braided layer in a distal portion of the guiding sheath shaft. Moreover, the hemostatic valve includes an improved friction ring with air vents to reduce the risk of air being introduced into the valve.

15 Claims, 6 Drawing Sheets

(51) Int. Cl.

| | |
|---|---|
| ***A61M 25/01*** | (2006.01) |
| ***A61M 39/06*** | (2006.01) |
| ***A61B 5/0538*** | (2021.01) |
| ***A61M 39/22*** | (2006.01) |
| ***D04C 3/40*** | (2006.01) |
| ***B29C 65/00*** | (2006.01) |
| *B29L 31/00* | (2006.01) |

(52) U.S. Cl.
CPC .... *A61M 25/0045* (2013.01); *A61M 25/0053* (2013.01); *A61M 25/0082* (2013.01); *A61M 25/0133* (2013.01); *A61M 25/0136* (2013.01); *A61M 25/0147* (2013.01); *A61M 39/0613* (2013.01); *A61M 39/223* (2013.01); *B29C 66/612* (2013.01); *D04C 3/40* (2013.01); *A61M 2039/062* (2013.01); *A61M 2039/229* (2013.01); *B29L 2031/7548* (2013.01)

(58) Field of Classification Search
CPC ............ A61M 25/0045; A61M 25/005; A61M 25/0136; A61M 25/0147; A61M 39/0613; A61M 39/223; A61M 2039/062; A61M 2039/229
See application file for complete search history.

(56) References Cited

U.S. PATENT DOCUMENTS 5,944,022 A 8/1999 Nardella et al.
5,983,126 A 11/1999 Wittkampf
6,456,864 B1 9/2002 Swanson et al.
7,536,218 B2 5/2009 Govari et al.
2004/0039369 A1 2/2004 Shelso
2004/0122360 A1 6/2004 Waldhauser et al.
2004/0181136 A1 9/2004 McDaniel et al.
2006/0129091 A1* 6/2006 Bonnette ................ A61B 17/22 604/93.01
2008/0091169 A1 4/2008 Heideman et al.
2009/0088725 A1* 4/2009 Bataille ............ A61M 25/0662 604/509
2012/0172717 A1* 7/2012 Gonda .................. A61B 5/042 600/424
2012/0277671 A1* 11/2012 Fuentes ............... A61M 25/005 604/95.04
2014/0323964 A1 10/2014 Leeflang et al.
2015/0088237 A1* 3/2015 Wechter ............... A61N 1/0539 607/116
2015/0217085 A1 8/2015 Haverkost et al.
2015/0343179 A1* 12/2015 Schumacher ...... A61M 25/0111 604/171
2016/0058971 A1* 3/2016 Leeflang .................. D04C 3/48 604/524
2017/0007310 A1* 1/2017 Rajagopalan ......... A61F 5/0079
2017/0080183 A1* 3/2017 Leeflang ........... A61M 25/0026

FOREIGN PATENT DOCUMENTS

CN 104367300 A 2/2015
JP 2001-518325 A 10/2001
JP 2016-137019 A 8/2016
WO WO 2010/099096 A1 9/2010
WO WO 2016/044854 A1 3/2016

OTHER PUBLICATIONS

Japanese Office Action for Application No. JP 2017-234020, dated Jun. 23, 2021 and English Translation (10 pages).
Translation of Chinese Search Report for Application No. CN 201711283933.6, dated Aug. 29, 2021, 3 pages.
Translation of First Office Action for Chinese Patent Application No. 201711283933.6, dated Jul. 9, 2021, 8 pages.
Second Office Action for Chinese Patent Application No. 201711283933.6, dated Jul. 3, 2022, 11 pages.
Chinese Supplemental Search for Application No. CN 2017112839336, dated Jan. 6, 2022, 1 page.
Translation of Notification of Reasons for Refusal for Japanese Patent Application No. 2017-234020, dated Jun. 29, 2021, 5 pages.
Written Opinion for Japanese Patent Application No. 2017-234020, dated Aug. 27, 2021, 6 pages.

* cited by examiner

STEERABLE GUIDING SHEATH WITH RING ELECTRODES AND RELATED METHOD OF CONSTRUCTION

FIELD OF INVENTION

This invention relates to a guiding sheath which is especially suitable for guiding electrophysiology catheter, in particular, a guiding sheath adapted for electrophysiology sensing and 3-D mapping.

BACKGROUND

Guiding sheaths are well known for use in facilitating pathway for a treatment or diagnostic catheter. Catheterization of the human heart often necessitates having a catheter gain access to the heart chambers, via a femoral vein and the aorta. To provide variation in movement, guiding sheaths (much like the catheters that are passed through the guiding sheaths) may be steerable or deflectable with the use of one or more puller wires for improved maneuverability in the patient's vasculature. However, because guiding sheaths have a sizable lumen defining the pathway for the catheter, available space within guiding sheaths, including lumen space for puller wires, is often limited. Moreover, the sizable lumen in the shaft of the guiding sheaths can lead to kinking and undesirable deflection characteristics.

Electrophysiology catheters are known to carry ring electrodes for sensing electrical signals within the patient's body, including electrical signals in the heart chamber in order to create 3-D electrophysiology maps representative of chamber anatomy and tissue electrical activity, such as for diagnosing cardiac arrhythmias. Such maps can also provide visualization of the location of the catheters, by displaying localized ring electrodes carried on the catheters, whose location/position is obtained through impedance or current-based measurements, where, for example, tissue impedance is measured between the ring electrodes on the catheter and patch electrodes placed on the patient's body surface. The position of the catheter is then derived from the impedance measurements. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, the entire disclosures of which are incorporated herein by reference.

While catheters may be so enabled to sense electrical signals for mapping and visualization, guiding sheaths are typically without such adaptations. Visualization of guiding sheaths is usually accomplished by fluoroscopy.

Guiding sheaths typically include a hemostatic valve extending from a control handle, to enable the introduction of a fluid into the shaft of the guiding sheath. Because of the fluid-tight seal of the hemostatic valve, the vacuum in the lumen of the sheath may draw or otherwise displace the catheter. While the hemostatic valve may include a friction ring adapted to releasably hold a catheter in place, the friction ring may inadvertently allow the introduction of air into the lumen when the catheter first enters the hemostatic valve.

Accordingly, there is a desire for a guiding sheath with improved pushability and deflection characteristics with minimal kinking or buckling. There is also desire for such guiding sheath to be enabled for electrical sensing, mapping and visualization via ring electrodes. In that regard, it is further desired for such guiding sheath to have improved shaft construction so that ring electrode lead wires can extend longitudinally along the shaft without interfering with pushability and deflection characteristics while remaining protected from electrical shorts, damage or breakage. There is a further desire that the hemostatic valve of the guiding sheath be configured to releasably hold a catheter in place while reducing the risk of air being introduced into the guiding sheath.

SUMMARY OF THE INVENTION

The present invention is directed to a guiding sheath with improved pushability and deflection characteristics with minimized risk of kinking or buckling for improved steerability and maneuverability. The guiding sheath is also equipped with ring electrodes for electrical sensing, mapping and visualization, along with improved shaft construction to protect ring electrode lead wires without interfering with shaft pushability and deflection. Moreover, the hemostatic valve of the guiding sheath is configured to releasably hold a catheter in place without the risk of air being introduced into the guiding sheath. In providing these features, the shaft of the guiding sheath is configured to use space efficiently without comprising the size of catheter pathway.

In some embodiments, the guiding sheath comprises an elongated shaft having an inner liner defining a lumen, a braided member with surrounding the inner liner, and an outer layer surrounding the braided member. The guiding sheath also includes at least one ring electrode mounted on the elongated shaft, at least one lead wire connected to the ring electrode, and a lumened tubing extending longitudinally along the shaft, the lumened tubing having a proximal portion, a transition portion, and a distal portion, the proximal portion extending below the braided member, the distal portion extending above the braided member, and the transition portion passing through an interstitial space or gap between fibers of the braided member.

In some embodiments, the braided member has a braided distal portion distal with a greater braid pitch and a braided proximal portion with a lesser braid pitch.

In some embodiments, the lumened tubing has a noncircular cross-section, for example, a generally rectangular cross-section.

In some embodiments, the lead wire extends nonlinearly along its length in the lumened tubing.

In some embodiments, the outer layer extending along the shaft has a distal portion and a proximal portion, the distal portion having a lesser durometer, and the proximal portion having a greater durometer.

In some embodiments, the braided member has interstitial spaces that are filled by a material of the outer layer.

In some embodiments, the guiding sheath further comprises a puller wire, and a puller wire tubing extending longitudinally along the shaft, the puller wire tubing extending below the braided member along the shaft.

In some embodiments, the guiding sheath further comprises a distal ring, wherein a distal end of the puller wire is affixed to the distal ring.

In some embodiments, the elongated shaft has a deflection section.

In some embodiments, the transition portion of the lumened tubing is proximal of the deflection section of the shaft.

In some embodiments, the guiding sheath further comprises a control handle and a hemostatic valve, the hemostatic valve having a friction ring with at least one air vent.

In some embodiments, the at least one air vent includes a radial indent.

In some embodiments, the at least one air vent includes a radial groove.

In some embodiments, a method of constructing a shaft of a guiding sheath, comprises providing an inner liner, and positioning a lumened tubing longitudinally alongside an outer surface of the inner liner. The method also includes forming a braided member with fibers, wherein for a first portion of the shaft, braiding the fibers over both the outer surface of the inner liner and a first portion of the lumened tubing, and wherein for a second portion of the shaft, braiding the fibers over the outer surface of the inner liner but under a second portion of the lumened tubing, and applying an outer layer over the inner liner, the braided fibers, and the lumened tubing.

In some embodiments, the method further comprises transitioning the lumened tubing at a junction between the first and second portions of the shaft so as to change or reposition the lumened tubing between being below the fibers and being above the fibers.

In some embodiments, the forming a braided member with fibers includes positioning the first portion of the lumened tubing in a first position relative to the inner liner and the fibers, braiding the fibers, stopping the braiding, after the stopping the braiding positioning the second portion of the lumened tubing in a second position relative to the inner liner and the fibers, and after the positioning the second portion of the lumened tubing resuming the braiding.

In some embodiments, the outer layer comprises a reflowable plastic material

In some embodiments, the applying an outer layer includes reflowing the outer layer.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
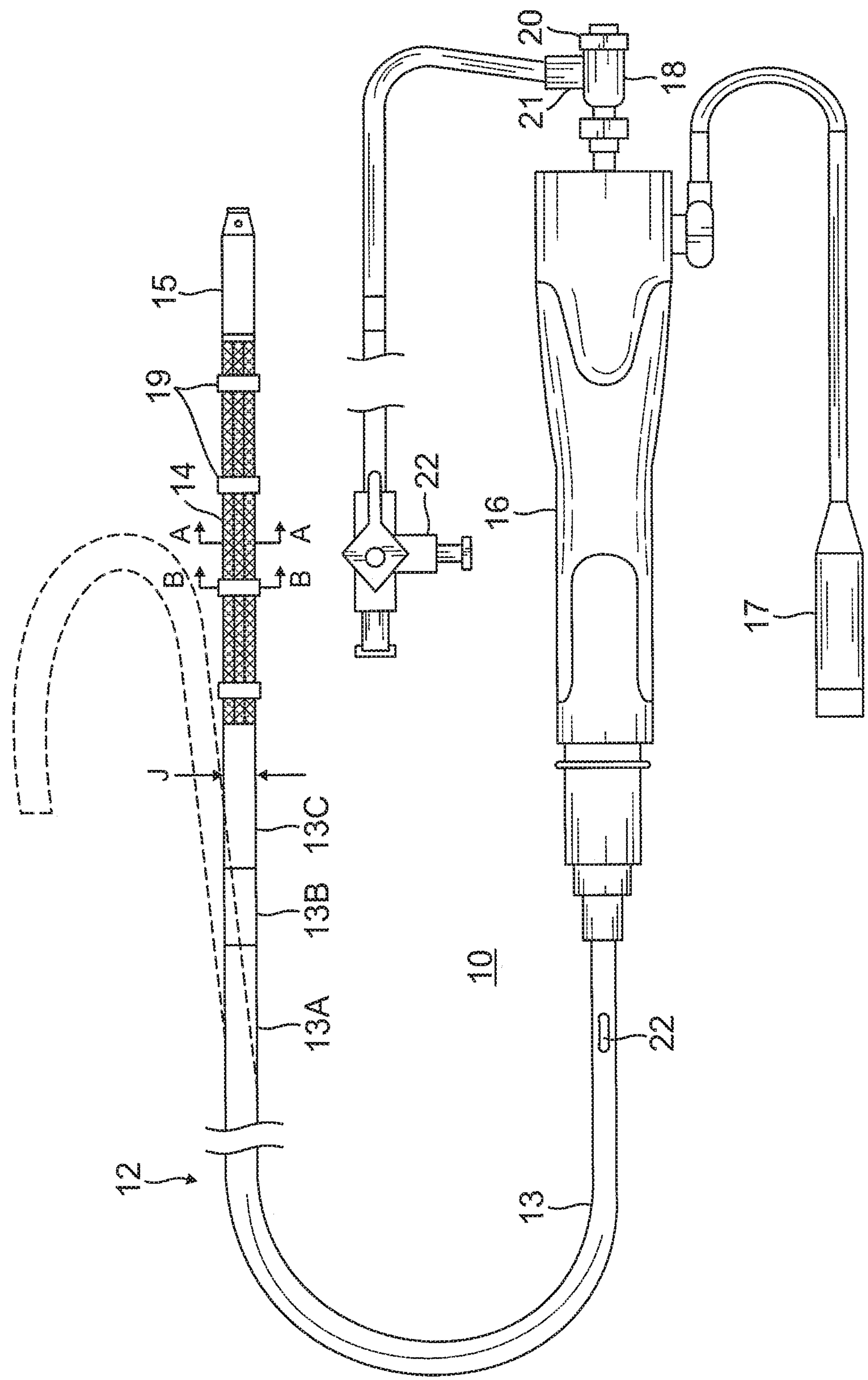
FIG. 1 is a top plan view of a guiding sheath, in accordance with an embodiment of the present invention.

Referring to FIG. 1, in some embodiment of present invention, a guiding sheath 10 includes an elongated and flexible shaft 12, and a control handle 16 proximal of the shaft 12. The shaft 12 includes a proximal section 13 and a distal deflection section 14, a distal tip section 15. The control handle 16 may be connected to an electrical connector 17 for transmitting electrical signals, as sensed by one or more ring electrodes 19 advantageously carried on the shaft 12, including, for example, the deflection section 14. The electrical signals are processed by a remote system (not shown), for example, a mapping system that provides visualization of portion(s) of the shaft 12 inside a patient's body based on impedance or current-based measurements, where impedance is measured between the ring electrodes 19 and patch electrodes (not shown) placed on the patient's body surface. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, the entire disclosures of which are incorporated herein by reference. The CARTO 3 mapping system, available from Biosense Webster, Inc., employs a hybrid technology using current-based data to also provide visualization of both sensor-based and non-sensor-based catheters and their electrodes. The hybrid system, called the Advanced Catheter Location (ACL) feature, is described in U.S. Pat. No. 7,536,218 to Govari et al., the entire disclosure of which is incorporated herein by reference.

Figure 2:
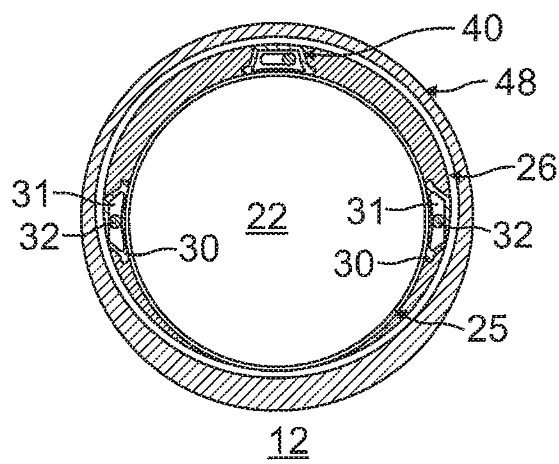
FIG. 2 is an end cross-sectional view of a shaft of the guiding sheath of FIG. 1, taken along line A-A

Also attached to the control handle 16, as shown in FIG. 1, is a hemostatic valve 18 having an end cap 20 adapted to receive a catheter (not shown) that can be advanced through a center lumen 22 of the guiding sheath 10, as shown in FIG. 2. The valve 18 also has side port 21 terminating in a luer hub, such as a two-way stop cock 22, for connection to one or more fluid sources (not shown) for providing fluid into and through the lumen 22 of the guiding sheath 10.

Figure 3B:
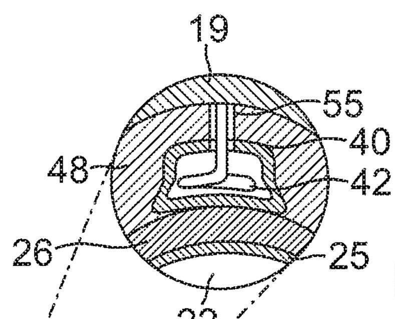
FIG. 3B is a detailed view of a lumened tubing of the guiding sheath of FIG. 3A.
Figure 3A:
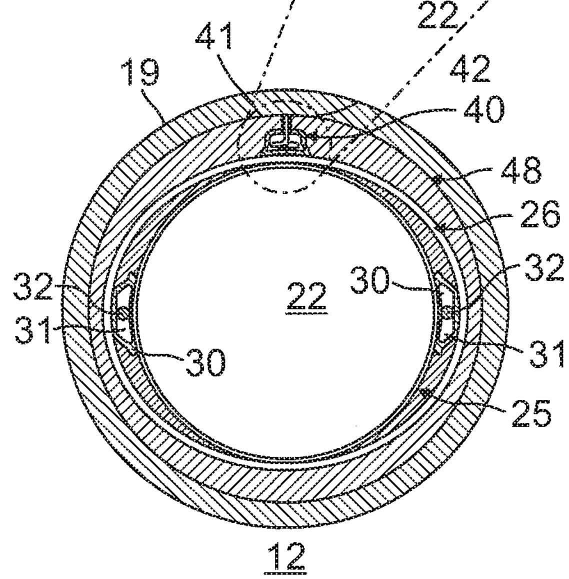
FIG. 3A is an end cross-sectional view of a shaft of the guiding sheath of FIG. 1, taken along line B-B.

Extending through the proximal portion 13 of the shaft 12, as shown in FIG. 2, and the distal deflection section 14, as shown in FIG. 3A, an inner tubing or liner 25 has a thin-wall construction defining the center lumen 22 of the shaft 12. The liner 25 may be constructed of any suitable material, including, for example, polytetrafluoroethylene (PTFE).

Figure 4:
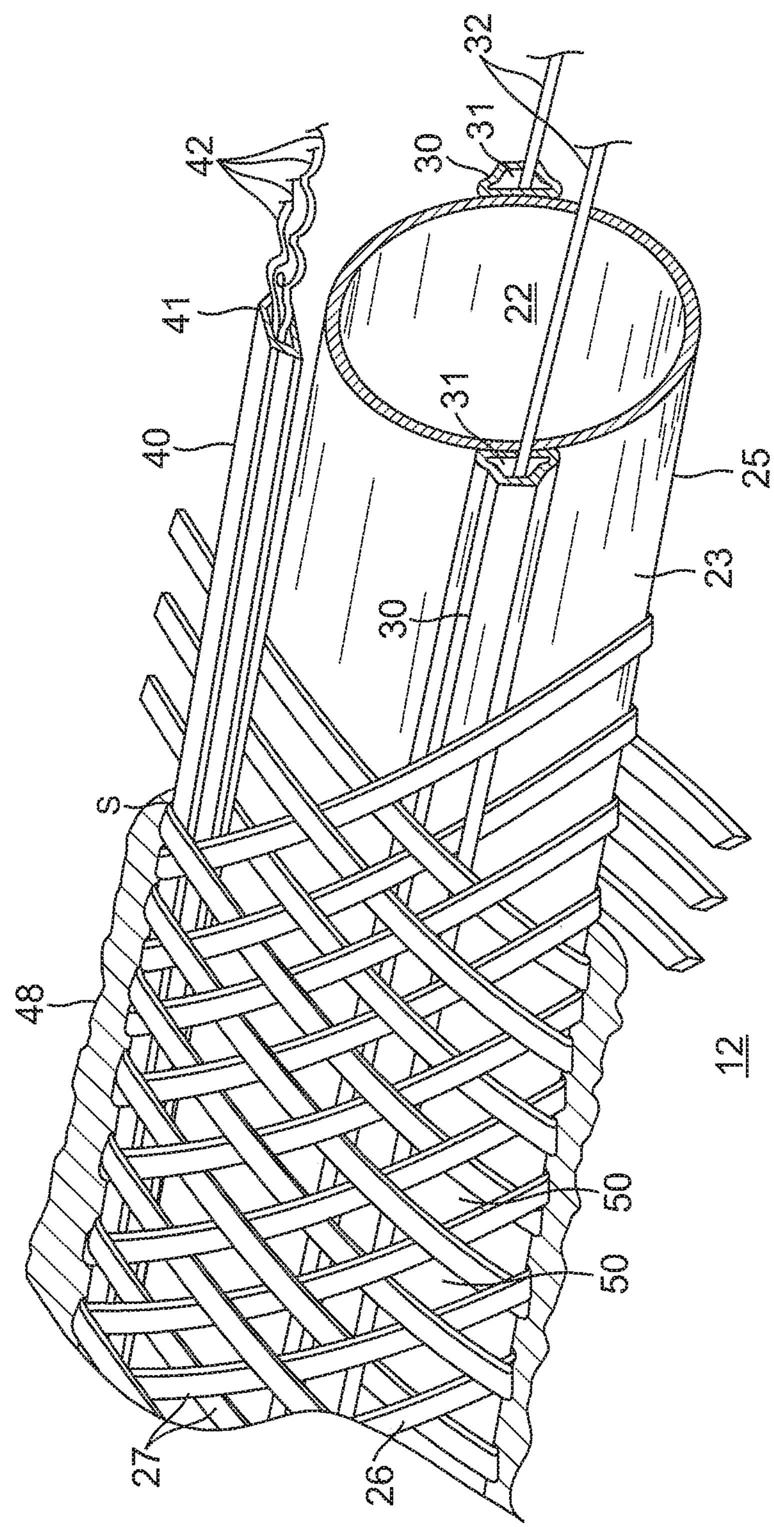
FIG. 4 is a representative perspective view of a shaft of the guiding sheath during assembly, with an outer layer shown partially applied, in accordance with an embodiment of the present invention.

Also with reference to FIG. 4, a variable braided member or layer 26 of braided strands or fibers 27 (separated by interstitial spaces or gaps 50 therebetween) extends around an outer surface 23 of the liner 25, generally surrounding the liner along its length to minimize kinking, wrinkling or buckling of the shaft 12. The braided layer 26 provides the shaft 12 with a balance of pushability and improved deflection characteristics. In some embodiments, the braided layer has a pitch ranging between about 20 and 50, and a pick per inch (PPI) ranging between about 50 and 22, preferably between about 45 and 27. The strands or fibers may be constructed of any suitable material, including, for example, high-strength stainless steel or high-strength polymer.

In some embodiments, the pitch and the PPI remain uniform throughout the entire length of the shaft 12. In other embodiments, the pitch and/or the PPI may be varied as appropriate or desired. For example, the braided layer 26 of the distal deflection section 14 may have a construction with about 45 PPI whereas the braided layer 26 of the proximal section 13 may have construction with about 27 PPI.

To enable deflection (either uni-directional or bi-directional) in the deflection section 14, one or two elongated puller wire tubings 30, each with a lumen 31 for a respective puller wire 32, extends longitudinally on the outer surface of the inner liner 25. Where two tubings 30 are provided, the lumened tubings 30 may be placed diametrically opposite of each other, across the lumen 22 for bi-directional deflection within a plane. As shown in FIG. 2, FIG. 3A and FIG. 4, the tubing(s) 30 may lie under the braided layer 26, for example, directly against the outer surface 23 of the liner 25 under the braided layer 26 for the entire length of the shaft 12. With the puller wire(s) 32 and tubing(s) 30 extending under the braided layer 26, the deflection section 14 has improved deflection characteristics.

Also extending longitudinally along the shaft 12 are one or more elongated lead wire tubings 40, each with a lumen 41 for one or more lead wires 42 and each lead wire connected to a respective ring electrode 19 for transmitting electrical signals sensed by the ring electrode 19. The one or more lumened tubings 40 are at radial locations different from radial locations of the one or more puller wire tubings 30. With reference to FIG. 2, FIG. 3A and FIG. 4, in the proximal portion 13 of the shaft 12, each tubing 40 lies under or below and surrounded by the braided layer 26, for example, lying directly against the outer surface of the inner liner 25. In the distal deflection portion 14 of the shaft 12, each tubing 40 lies above or outside of the braided layer 26. A junction J defines a location of a transition portion of each tubing 40 that transitions between below and above the braided layer 26. Although FIG. 4 illustrates generally uniform braiding at the junction J around the transition portion of the tubing 40, it is understood that the pitch and/or PPI may be varied to accommodate the transition portion, resulting in a larger interstitial space or gap at location S between the strands or fibers 27 of the braided layer 26 where the tubing 40 extends through the braided layer 26.

The transition of the tubing 40 between outside or inside of the braided layer 26 advantageously allows the lead wires 42 to be connected to the ring electrodes 19 carried on the shaft 12 in balancing a variety of competing factors, including, for example, ease of manufacturing and assembly, protection of the lead wires from damage, space efficiency and radial symmetry of the shaft.

Figure 5A:
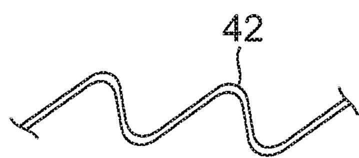
FIG. 5A is a perspective view of a portion of a lead wire, in accordance with an embodiment of the present invention.
Figure 5B:
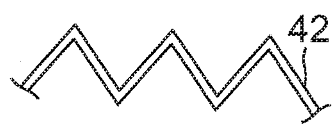
FIG. 5B is a perspective view of a portion of a lead wire, in accordance with an embodiment of the present invention.
Figure 5C:
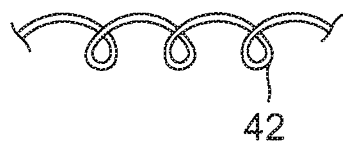
FIG. 5C is a perspective view of a portion of a lead wire, in accordance with an embodiment of the present invention.

Extending through the lumen 41, the lead wires 42 are advantageously configured with a nonlinear pattern to provide excess length relative to the length of the tubing 40 and the shaft 12 so as to provide the lead wires with a degree of slack and "give" in avoiding breakage when the shaft 12 is deflected, especially when deflected repeatedly. The nonlinear pattern may include, for example, a serpentine (FIG. 5A), a zig-zag (FIG. 5B), a coil (FIG. 5C) or combinations thereof. The lead wires 42 may also be wrapped around a mandrel or any suitable support structure which would also avoid breakage during deflection.

Figure 8:
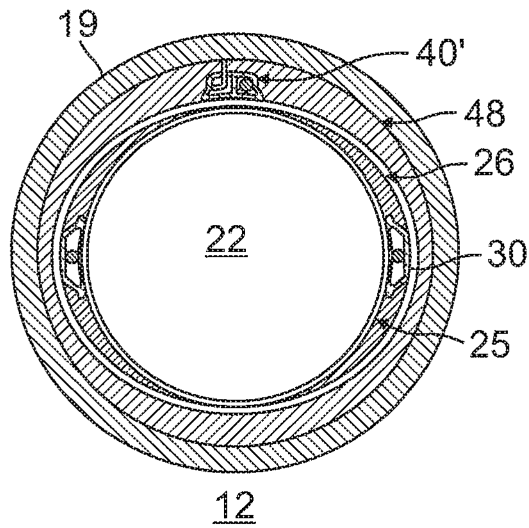
FIG. 8 is an end cross-sectional view of a shaft of FIG. 7, with a ring electrode.
Figure 7:
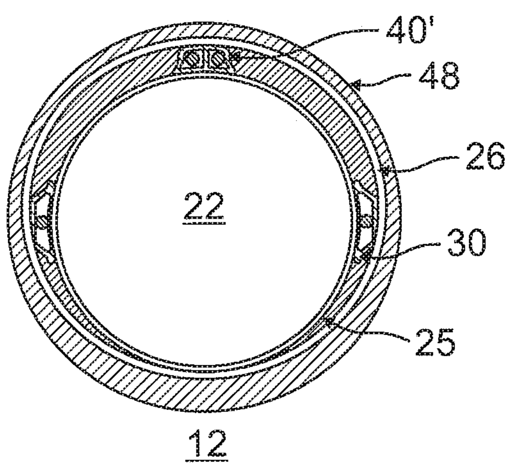
FIG. 7 is an end cross-sectional view of a shaft, in accordance with another embodiment of the present invention.

In other embodiments, the guide wire tubing 40 may also be multi-lumened, as shown in FIG. 7 and FIG. 8, for additional lead wires or other suitable components.

Each of the tubings 30 and 40 has a noncircular cross-section so as to minimize the overall outer diameter of the shaft 12 while providing a sufficiently large lumen 22 for housing the components therein. For example, the cross-section of the tubings is characterized by a major-axis-to-minor-axis ratio greater than about 2:1.

The shaft 12 along its length includes an outer layer or coating 48 that extends over braided layer 26 and seals all the underlying components. The outer layer 48 comprises a material that is applied in a manner that allows the material to seep, for example, by reflowing, over the tubings 30 and 40, and between the strands or fibers 27 of the braided layer 26 and generally fill the interstitial spaces 50 therein. The tubings 30 and 40, the braided layer 26 and also a distal ring 45 are embedded in the outer layer 48. Suitable material for the outer layer 48 includes, for example, polyphthalamide, such as VESTAMID, and/or polyether block amide, such as PEBAX.

The outer layer 48 may comprise materials of different durometer for different sections of the shaft 12 in providing different deflection characteristics, including, for example, a "C" curve or a "U" curve (see FIG. 1). In the embodiment of FIG. 1, the shaft 12 has a first (most) proximal section 13A with an outer layer constructed of VESTAMID, a second proximal section 13B with an outer layer constructed of PEBAX 6333, a third proximal section 13C with an outer layer constructed of PEBAX 5583, a distal section 14 with an outer layer constructed of 50% PEBAX/50% PEBAX 4533. To enable deflection of the shaft 12, durometer of the outer layer 48 (the sections thereof) decreases from its proximal end to its distal end. In other words, flexibility of the outer layer 48 increases from its proximal end to its distal end along the length of the shaft 12.

Each lead wire 42 is connected to its respective ring electrode 19. As shown in FIG. 3B, an aperture 55 is formed through the outer layer 48 and the tubing 40 so that a lead wire 42 can pass from inside the lumen 41 to outside of the outer layer 48 for connection to a respective ring electrode 19. The lead wires 42 transmit electrical signals sensed by the ring electrodes 19 to the remote system via the electrical connector 17 proximal of the control handle 16, as shown in FIG. 1.

Figure 6:
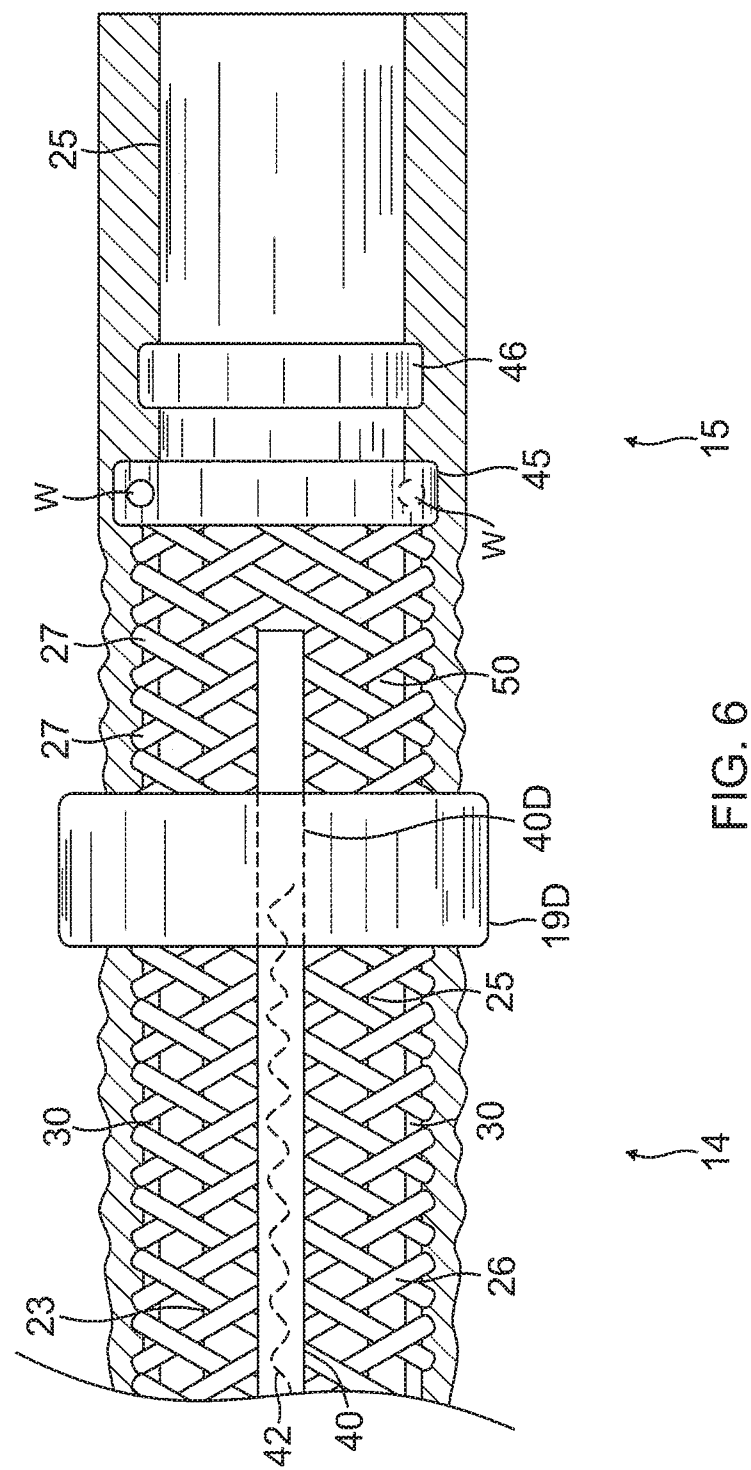
FIG. 6 is a top plan view of a distal tip section of the shaft of the guiding sheath, with the outer layer partially broken away, in accordance with an embodiment of the present invention.

In the illustrated embodiment, the lead wire tubing 40 has a distal end between the distal-most ring electrode 19D and the distal ring 45. In the embodiment of FIG. 6, the tubing 40 has a lead wire 42D for the distal-most ring electrode 19D. Each puller wire tubing 30 has a distal end that is also between the distal-most ring electrode 19D and the distal ring 45. A distal end of each puller wire 32 emerging from a distal end of a respective tubing 30 is fixedly attached to and anchored by the distal ring 45 mounted on the inner liner 25, distal of the distal-most ring electrode 19D. The distal end of each puller wire 32 may be affixed to the ring 45 by any suitable method, including welding, as shown at W. The distal ring 45 has an inner diameter slightly larger than the outer diameter of the braided layer 26 so that it can surround and secure a distal end of the braided layer 26 onto the inner liner 25. The distal ring 45 has an outer diameter less than the outer diameter of the outer layer 48, so that the distal ring is embedded in the outer layer 48. A radiopaque marker, e.g., distal ring 46, may be provided to visually indicate the distal end of the shaft under fluoroscopy.

In some embodiments of the present invention, a method for manufacturing the shaft 12 of the guiding sheath 10 includes:

a) providing an inner liner, b) positioning a lumened tubing (for example, a lead wire tubing) longitudinally alongside an outer surface of the inner liner, c) forming a braided member or layer with fibers, wherein i) for a first or proximal portion of the shaft, braiding the fibers over both the outer surface of the inner liner and a first or proximal portion of the lumened tubing, ii) for a second or distal portion of the shaft, braiding fibers over the outer surface of the inner liner but under a second or distal portion of the lumened tubing, and d) applying an outer layer over the inner liner, the braided fibers, and the lumened tubing along a length of the shaft.

The method may include transitioning the lumened tubing at a junction between the first and second portions of the shaft so as to change the position of lumened tubing relative to the braided member, for example, between being below the fibers and being above the fibers.

In more detailed embodiments, the method may include the following:

a) positioning the first portion of the lumened tubing in a first position relative to the inner liner and the fibers, b) braiding the fibers, c) stopping the braiding, d) after the stopping the braiding, positioning the second portion of the lumened tubing in a second position relative to the inner liner and the fibers, and e) after the positioning the second portion of the lumened tubing, resuming the braiding.

It is understood that the braiding may begin at a distal end of the shaft and progress toward a proximal end of the shaft, or vice versa, as desired or appropriate. Accordingly, the lumened tubing may be moved or adjusted during braiding of the fibers from being above the braided member to being under the braided member, or vice versa.

The braiding the fibers may include braiding the fibers with a first braid pitch, and the resuming braiding the fibers may include braiding the fibers with a second braid pitch different from the first braid pitch.

The method may also include passing a nonlinear lead wire through the lumened tubing, wherein the lead wire has a nonlinear configuration, for example, serpentine, zigzag, or coil.

The method may further include:

a) positioning a puller wire lumened tubing longitudinally alongside the outer surface of the inner liner, b) braiding the fibers over the puller wire lumened tubing and the inner liner, wherein i) for a first or proximal portion of the shaft, braiding the fibers over both the outer surface of the inner liner and a proximal portion of the lumened tubing, ii) for a second or distal portion of the shaft, braiding the fibers over the outer surface of the inner liner but under a second or distal portion of the lumened tubing, and d) applying an outer layer over the inner liner, the braided fibers, and the lumened tubing.

The applying an outer layer over the inner liner, the braided fibers, and the lumened tubing may include reflowing the outer layer wherein the outer layer comprises a reflowable plastic or thermoplastic material. Reflowing the outer layer allows the material to seep between the fibers, filling the interstitial spaces between the fibers of the braided member. As mentioned herein, the outer layer of different sections of the shaft may comprise reflowable plastic or thermoplastic of different durometer.

The method may also include:

a) providing a distal ring at or near a distal end of the inner liner, where a distal end of a puller wire is affixed to the distal ring; and b) applying the outer layer over the distal ring.

Figure 9:
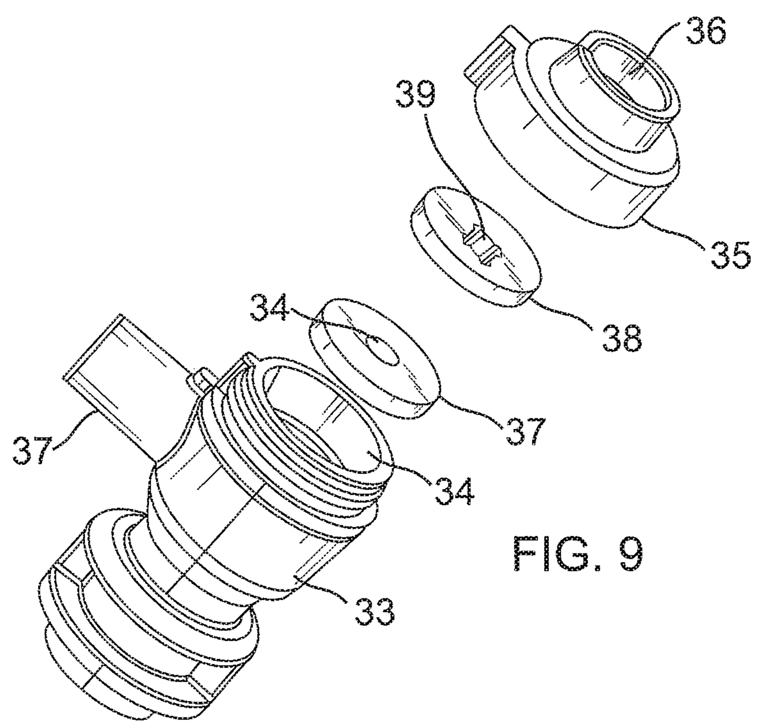
FIG. 9 is an exploded perspective view of a hemostatic valve with a friction ring, in accordance with an embodiment of the present invention.

As shown in FIG. 1 and FIG. 9, the hemostatic valve 18 proximal of the control handle 16 includes a hub housing 33 with a central passage 34 through which a catheter or like device (not shown) may be passed. The housing 33 is configured with a side port 37 that is in communication with the central passage 34 for enabling passage of a fluid (e.g., saline) from a remote source (not shown) into the central passage 34 and distally through the shaft 12. The valve 18 includes an end cap 35 mounted on a proximal end of the hub housing 33. The end cap 35 has a central opening 36 that defines an entry into the central passage 34. Positioned in the central passage 34, distal of the opening 36 of the end cap 35, is a seal valve member 37 having a disc configuration corresponding in size and shape to the circular cross-sectional shape and size of the central passage 34 to block and seal the central passage with the exception of a deformable center opening 34 (e.g., one or more slits) that remains closed or sealed in a neutral configuration (to prevent fluid from leaking out of the valve 18), except under load of a distal end of a catheter or like device (used interchangeably herein) being advanced distally into the guiding sheath 10.

The valve 18 also includes a friction ring 38 to releasably hold a catheter inserted into the guiding sheath. The friction ring 38 is configured as a washer with a center passage 39 to receive a catheter. In the illustrated embodiment, the friction ring 38 and the seal valve member 37 are arranged in abutting contact with each other, with the friction ring 38 distal of the seal valve member 37 and positioned between the seal valve member 37 and the end cap 35. The center passage 39 of the friction ring 38 is axially aligned with the deformable opening 34 of the seal valve member 37 so that a catheter passes through both the deformable opening 34 and the center passage 39 when inserted into the valve 18. In that regard, both the seal valve member 37 and the friction ring 38 are constructed of a deformable, elastic material. However, while the deformable opening 34 of the seal valve member 37 is configured to remain closed when there is no load, the center passage 39 of the friction ring 38 is configured to remain open and has a radius sized according to the french size(s) of the catheter suitable for use with the guiding sheath so that the catheter is movable through the center passage 39 but is held in place relative to the valve 10 by circumferential frictional contact with the periphery of the center passage 39 of the friction ring 38 whenever a user releases his grasp of the catheter.

Figure 10:
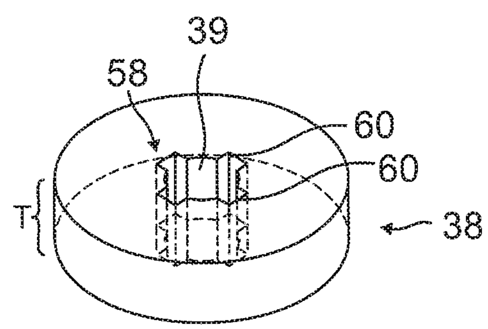
FIG. 10 is a perspective view of the friction ring of FIG. 9.

When a catheter is introduced into the valve 18 and advanced past the central opening 36 of the end cap 35, a distal end of the catheter entering the central passage 39 of the friction ring 38 can displace the air occupying the central passage 39. To prevent the displaced air from passing distally through the center opening 34 of the seal valve member 37, the friction ring 38 is advantageously configured with one or more air vents 58 that direct the displaced air to move away from the center opening 34 of the seal valve member 37. In the illustrated embodiment of FIG. 10, the air vents include one or more radial indents 60 provided around the central passage 39 which are space voids free from contact with the catheter extending through the central passage 39 and thus allow the displaced air to vent radially through the radial indents 60 and then proximally away from the center opening 34. The radial indents 60 extend through the entire thickness T of the friction ring 38 in the longitudinal direction. In the illustrated embodiment, the radial indents 60 are arranged in diametrical pairs around the central passage 39.

Figure 11:
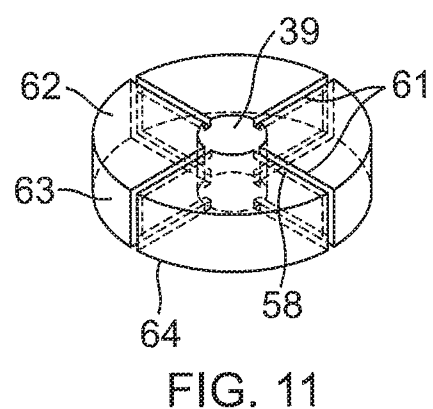
FIG. 11 is a perspective view of a friction ring, in accordance with an embodiment of the present invention.

In the illustrated embodiment of FIG. 11, the air vents 58 include one or more radial grooves 61 formed in a proximal surface 62, an outer circumferential surface 63 and an outer distal surface 64 of the friction ring 38. In the illustrated embodiment, the radial grooves 61 are arranged in diametrical pairs around the central passage 39.

It is understood that where the hemostatic valve 18 is of a Tuohy-Borst type with a threaded end cap, the end cap can be adjusted to increase or decrease compression of the seal valve member 37 and/or the friction ring 38 to allow adjustment of the friction grip exerted by the seal valve member 37 and/or the friction ring 38 on the catheter passing therethrough.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings and relative dimensions are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A guiding sheath, comprising:

an elongated shaft having an inner liner defining a lumen, a braided member surrounding the inner liner, and an outer layer surrounding the braided member;

a ring electrode mounted on the elongated shaft;

a lead wire having a distal end connected to the ring electrode;

a lumened lead wire tubing extending longitudinally along the elongated shaft, the lumened lead wire tubing having a proximal portion, a transition portion, and a distal portion, the proximal portion extending below the braided member, the distal portion extending above the braided member, and the transition portion passing through a gap in the braided member, the lead wire extending longitudinally through the lumened lead wire tubing;

a puller wire;

a lumened puller wire tubing in contact with and extending longitudinally along the elongated shaft, the lumened puller wire tubing extending below the braided member along its entire length, and the puller wire extending longitudinally through the the lumened puller wire tubing;

a control handle at a proximal end of the elongated shaft; and a hemostatic valve proximal of the control handle, the hemostatic valve comprising:

a hub housing comprising proximal and distal ends and a central passage, an end cap mounted on the proximal end of the hub housing and comprising a central opening defining an entry into the central passage of the hub housing, a seal valve member positioned within the central passage of the hub housing and comprising a deformable central opening, the deformable central opening being configured to remain closed in a neutral configuration but to deform upon exertion of axial pressure on the deformable central opening by a device to allow passage of the device when the device is extended through the central passage, and a friction ring positioned within the central passage of the hub housing distal of the seal valve member and comprising a central aperture that remains open and is axially aligned with the deformable opening of the seal valve member, the central aperture of the friction ring configured for frictional contact with the device when the device is extended through the central passage, and configured to minimize passage of air distally from the central opening of the seal valve member as the device is extended through the central passage.

2. The guiding sheath of claim 1, wherein the braided member has a braided distal portion distal of the gap and a braided proximal portion proximal of the gap, the braided distal portion has a first pitch and the braided proximal portion has a second pitch that is lesser than the first pitch.

3. The guiding sheath of claim 1, wherein the lumened lead wire tubing has a noncircular cross-section.

4. The guiding sheath of claim 3, wherein the lumened lead wire tubing has a generally rectangular cross-section.

5. The guiding sheath of claim 1, wherein the lead wire extends nonlinearly along its length in the lumened lead wire tubing.

6. The guiding sheath of claim 1, wherein the outer layer has a distal portion and a proximal portion, the distal portion having a first durometer, and the proximal portion having a second durometer that is greater than the first durometer.

7. The guiding sheath of claim 1, wherein the braided member has interstitial spaces that are filled by a material of the outer layer.

8. The guiding sheath of claim 1, wherein the guiding sheath further comprises:

a second puller wire; and a second puller wire tubing extending longitudinally along the shaft, the second puller wire tubing extending below the braided member along its entire length.

9. The guiding sheath of claim 1, further comprising a distal ring, wherein a distal end of the puller wire is affixed to the distal ring.

10. The guiding sheath of claim 1, wherein the elongated shaft has a deflection section.

11. The guiding sheath of claim 10, wherein the gap in the braided member is proximal of the deflection section.

12. The guiding sheath of claim 1, wherein the central opening of the friction ring comprises at least one air vent.

13. The guiding sheath of claim 12, wherein the at least one air vent includes a radial indent.

14. The guiding sheath of claim 12, wherein the at least one air vent includes a radial groove.

15. The guiding sheath of claim 1, wherein the lumened lead wire tubing comprises a plurality of lumens.

* * * * *